United States Patent
Bottenus (10) Patent No.: US 12,201,480 B2
(45) Date of Patent: Jan. 21, 2025

(54) DECODING MULTIPULSE ULTRASOUND DATA

(71) Applicant: The Regents of the University of Colorado, a body, Denver, CO (US)

(72) Inventor: Nick Bottenus, Erie, CO (US)

(73) Assignee: The Regents of the University of Colorado, a body corporate, Denver, CO (US)

(*) Notice: Subject to any disclaimer, the term of this patent is extended or adjusted under 35 U.S.C. 154(b) by 0 days.

(21) Appl. No.: 18/682,261

(22) PCT Filed: Aug. 30, 2022

(86) PCT No.: PCT/US2022/041988
§ 371 (c)(1),
(2) Date: Feb. 8, 2024

(87) PCT Pub. No.: WO2023/034263
PCT Pub. Date: Mar. 9, 2023

(65) Prior Publication Data
US 2024/0260943 A1    Aug. 8, 2024

Related U.S. Application Data

(60) Provisional application No. 63/272,155, filed on Oct. 26, 2021, provisional application No. 63/238,769, filed on Aug. 30, 2021.

(51) Int. Cl.
*A61B 8/00*   (2006.01)
*A61B 8/08*   (2006.01)
*G01S 7/52*   (2006.01)

(52) U.S. Cl.
CPC .......... *A61B 8/5207* (2013.01); *A61B 8/4488* (2013.01); *A61B 8/54* (2013.01); *G01S 7/52026* (2013.01); *G01S 7/5209* (2013.01)

(58) Field of Classification Search
CPC .................................................. A61B 8/5207
See application file for complete search history.

(56) References Cited

U.S. PATENT DOCUMENTS 10,064,602 B2   9/2018   Ustuner et al.
10,194,889 B2   2/2019   Hollender et al.
(Continued)

OTHER PUBLICATIONS

Ehsan Abadi, William P. Segars, Benjamin M. W. Tsui, Paul E. Kinahan, Nick Bottenus, Alejandro F. Frangi, Andrew Maidment, Joseph Lo, Ehsan Samei, "Virtual clinical trials in medical imaging: a review," J. Med. Imag. 7(4) 042805 (Apr. 11, 2020) https://doi.org/10.1117/1.JMI.7.4.042805.
(Continued)

*Primary Examiner* — Joseph M Santos Rodriguez
(74) *Attorney, Agent, or Firm* — McGaw Law, P.C.; Michael M. McGaw (57) ABSTRACT

Diagnostic imaging of deep targets in the body requires sufficient signal amplitude to overcome effects such as attenuation with depth and thermal noise produced in signal reception. Coded excitation provides several strategies to increase the total transmitted energy without exceeding peak amplitude safety limits. Temporal coding has proven particularly effective, but these frequency or amplitude modulation techniques require additional transmit capabilities and often require complex processing to reduce decoding artifacts. An alternative code is presented based on time delays that relies on repeated transmit pulses that can be decoded using spatiotemporal synthetic aperture processing. A 16-pulse code is demonstrated that achieves an 11.1 dB improvement in signal-to-noise ratio (SNR) while maintaining axial resolution and sufficient range lobe performance. Further, a beamforming strategy for multiline transmission ultrasound data is presented that recognizes the data as time delay encoded and performs an appropriate decoding to
(Continued)

reduce common reconstruction artifacts. This approach simultaneously enables synthetic aperture focusing of multiline transmission data, improving focusing through depth.

23 Claims, 6 Drawing Sheets

(56) References Cited

U.S. PATENT DOCUMENTS

| | | |
|---|---|---|
| 10,349,917 B2 | 7/2019 | Boctor et al. |
| 10,969,487 B2 | 4/2021 | Trahey et al. |
| 11,583,254 B2 | 2/2023 | Bottenus et al. |
| 2018/0275272 A1 | 9/2018 | Questa |
| 2020/0183004 A1 | 6/2020 | Gong et al. |
| 2020/0284902 A1 | 9/2020 | Kruse |

OTHER PUBLICATIONS

Bottenus N. Recovery of the Complete Data Set From Focused Transmit Beams. IEEE Trans Ultrason Ferroelectr Freq Control. Jan. 2018;65(1):30-38. doi: 10.1109/TUFFC.2017.2773495. PMID: 29283345; PMCID: PMC5768147.

DECODING MULTIPULSE ULTRASOUND DATA

CROSS-REFERENCE TO RELATED APPLICATIONS

This application claims the benefit of U.S. Provisional Application No. 63/238,769, filed Aug. 30, 2021 and U.S. Provisional Application No. 63/272,155, filed Oct. 26, 2021.

FIELD OF INVENTION

This invention relates to ultrasound imaging systems and methods. More particularly, this invention relates to methods and devices for decoding multipulse ultrasound data.

BACKGROUND OF THE INVENTION

Ultrasound is an invaluable tool for noninvasive diagnosis in the heart, observing anatomy and function at the patient bedside. However, inadequate visualization of the heart is common. In one study, 41% of patients with suspected coronary artery disease had inadequate visualization of the left ventricle. In another, 42% of postsurgical patients had inadequate visualization of one ventricle. Obesity also presents problems in visualization with reduced acoustic penetration and added image clutter.

SUMMARY OF THE INVENTION

The present invention provides an approach to ultrasound imaging that enables both higher image quality (increased signal-to-noise ratio, SNR) and faster image acquisition. This innovation has two complementary components; (1) a multipulse acoustic transmission and (2) a decoding of the time-delay encoded data before geometric focusing. This approach should be compatible with a wide range of modern clinical scanner platforms as it relies on repetition of the standard output pulse and access to array data for decoding, which is an emerging technology used by manufacturers.

SNR represents a fundamental limitation in all applications of ultrasound, restricting the achievable image resolution and penetration depth. The FDA prescribes limits restricting the peak acoustic output, so a signal can only be increased by increasing pulse duration (total energy) rather than increasing pulse amplitude. Common approaches, such as chirp transmissions or coded excitations (e.g. Barker, Golay), have significant limitations that hinder clinical translation, including requiring complex transmission systems or incompatibility with harmonic imaging; a clinical standard in cardiology. The approach taught herein involves transmitting the same output pulse multiple times, such as with varying time delays, in rapid succession. The resulting echoes can be decoded using the methods taught herein to recover good resolution with high SNR, even in harmonic mode.

Frame rate is a second major consideration in clinical imaging, especially in the heart where fast-moving events need to be recorded. Emerging 3-D imaging technologies suffer even worse than 2-D imaging as more transmissions are needed to cover the imaging volume. Multi-line transmission provides a solution, sending sound in multiple directions at once to reduce the number of total transmissions required. This multiline transmission approach results in cross-talk between image lines, degrading image contrast. The multipulse approach taught herein involves transmitting sound in multiple directions at once and decoding the resulting echoes using the applied transmit time delays. Compared to conventional dynamic receive methods this decoding method produces higher quality images (resolution, target detectability, SNR) at the accelerated frame rate provided by multi-line transmission.

One approach is to employ a decoding strategy to reconstruct ultrasound images with improved resolution through depth compared to conventional images. This technique extends that approach to multipulse transmissions, enabling a much broader design space for imaging sequence design. The disclosed techniques are demonstrated herein in simulation and phantom imaging that both higher SNR and frame rate can be achieved for a typical cardiac imaging sequence. In one experiment, 4× faster acquisition was achieved with 1.5× to 2.5× improvement in SNR.

These tools should prove particularly useful to ultrasound manufacturers, particularly for those developing cardiac ultrasound imaging platforms. The techniques taught herein can be implemented as a software enhancement for B-mode cardiac imaging, but should be useful in other diagnostic applications as well (e.g., general radiology and OB/GYN applications). The enhancements should prove compatible with a wide range of ultrasound transducers, imaging modes, and post-processing techniques in use by these manufacturers.

Diagnostic ultrasound typically uses short pulses transmitted on array elements. These pulses are time-delayed to focus sound spatially. In some applications, these transmit pulses may be repeated or modified to produce a temporal coding. The invention describes this as a linear system (i.e., time delays, weighting, and summation). The invention applies an inverse filter based on this linear system across multiple transmissions (e.g., steering angles). The following are two demonstrations of this technique with different multiple-pulse transmission schemes: (1) Pulses can be modified using an amplitude or frequency coding to output more total energy, improving depth penetration of the ultrasound wave. These codes must be designed to be decoded to recover a short transmit pulse and often are subject to artifacts in decoding. The invention allows for increased acoustic output using repeated identical pulses (or with weightings) by applying the inverse filter across an imaging sequence of varied steering angles or focal points. This allows for a simpler ultrasound transmit system and more sequence flexibility than in the typical amplitude/frequency coding case. (2) Multiline transmit encoding has been proposed to send sound in multiple directions during one ultrasound pulse-echo event, speeding up acquisition in applications like cardiac imaging. Each direction requires an additional time-delayed pulse in the transmit event. Image formation then relies on separating the multiple transmit beams using receive focusing, resulting in cross-talk artifacts between the multiple steering directions. The invention describes this transmission using a linear system and allows for synthetic aperture focusing of these data, improving signal-to-noise ratio and resolution in a way not possible with existing image formation methods. The present invention provides inverse filtering of multiple transmitted pulses across transmissions (decoding a 2-D encoding, in contrast to a 1-dimensional inverse filter used in some temporal codes). This will provide improved pulse sequence design and array beamforming for signals for multiple-pulse transmissions. This enables improved wave penetration (i.e., deeper imaging) or faster imaging.

Some aspects of the present invention include the pairing of the transmit sequence that uses multiple pulses per transmission with the decoding methodology. Methods employing a single transmitted pulse often achieve synthetic focusing without the improvements in SNR or acquisition time that this invention enables.

In certain aspects a decoding method can then be employed using a regularized pseudoinversion, whereas while the previous specifically referenced an adjoint operation.

In a first aspect the present invention provides a first method for ultrasound imaging of a target region. The method according to the first aspect includes the steps of (1) providing an ultrasound system having an ultrasound transducer array with a plurality of ultrasound elements on the transducer array; (2) transmitting an ultrasound transmission from at least a subset of the plurality of elements of the transducer array to the target region; (3) receiving a plurality of echo signals at each of the subset of the plurality of elements of the array, each echo signal being responsive to the emitted pulses; (4) applying a decoding function based on the applied time delays to at least some of the subset of the plurality of echo signals received at corresponding elements of the array; (5) modifying the defined time delays and repeating steps (2)-(4) to provide an ultrasound dataset representing a recovered source element domain of the ultrasound dataset; (6) focusing and beamforming the ultrasound dataset to map time signals of the ultrasound dataset and combine channel signals to provide spatial pixel data; and (7) forming an ultrasound image from the spatial pixel data. The transmission in the transmitting step comprises a plurality of pulses and multiple pulses will be employed for methods according to the first aspect. Successive pulses within a transmission are emitted with a defined time delay. The time delay can vary between at least some of the pulses or the time delay can remain the same for pulses within a particular transmission. Each pulse in a particular transmission is emitted from at least a subset of the plurality of elements of the transducer array. In an advantageous embodiment the time delays of each of the plurality of elements forms a time delay encoding matrix. The time delay encoding matrix can comprises delays for focused, plane or diverging transmissions. In further embodiments time delay encoding matrix can employ randomly generated time delay values. Post-processing can be applied to the recovered source element domain of the ultrasound dataset. In certain embodiments, the time delay encoding matrix is modified to avoid overlapping pulse excitations in time.

As mentioned above, in an advantageous embodiment the time delays of each of the plurality of elements forms a time delay encoding matrix. A number of methods can be utilized to implement time delays between the repeated pulses and across the transmitting elements (forming a 2-D matrix). One possible method is to determine time delays using geometric models. Alternatively, random delays can be used. Random delays produce a numerically advantageous encoding. One issue with some models is that they may demand pulses be generated with a smaller delay than can be physically realized on a given ultrasound system. Modifying the time delay matrix can be accomplished to avoid overlapping pulse excitations in time, proposes, for example, that one modifies these models to enforce some minimum time delay. The described invention is compatible with such modifications and such modifications may facilitate implementation on certain systems. For example, in FIG. 6 the edge array elements each transmit three non-overlapping pulses. In contrast the center elements have overlapping pulses. Overlapping pulses can be analogized to repeatedly striking a bell while the bell is ringing. If each pulse/strike takes some time, a delay encoding can be used to avoid striking faster than that time. To avoid complications, one can lengthen the specified delay to that minimum time, or potentially change it in other ways (e.g., add a random time to it to avoid exactly repeating delay values between pulses).

Figure 10:
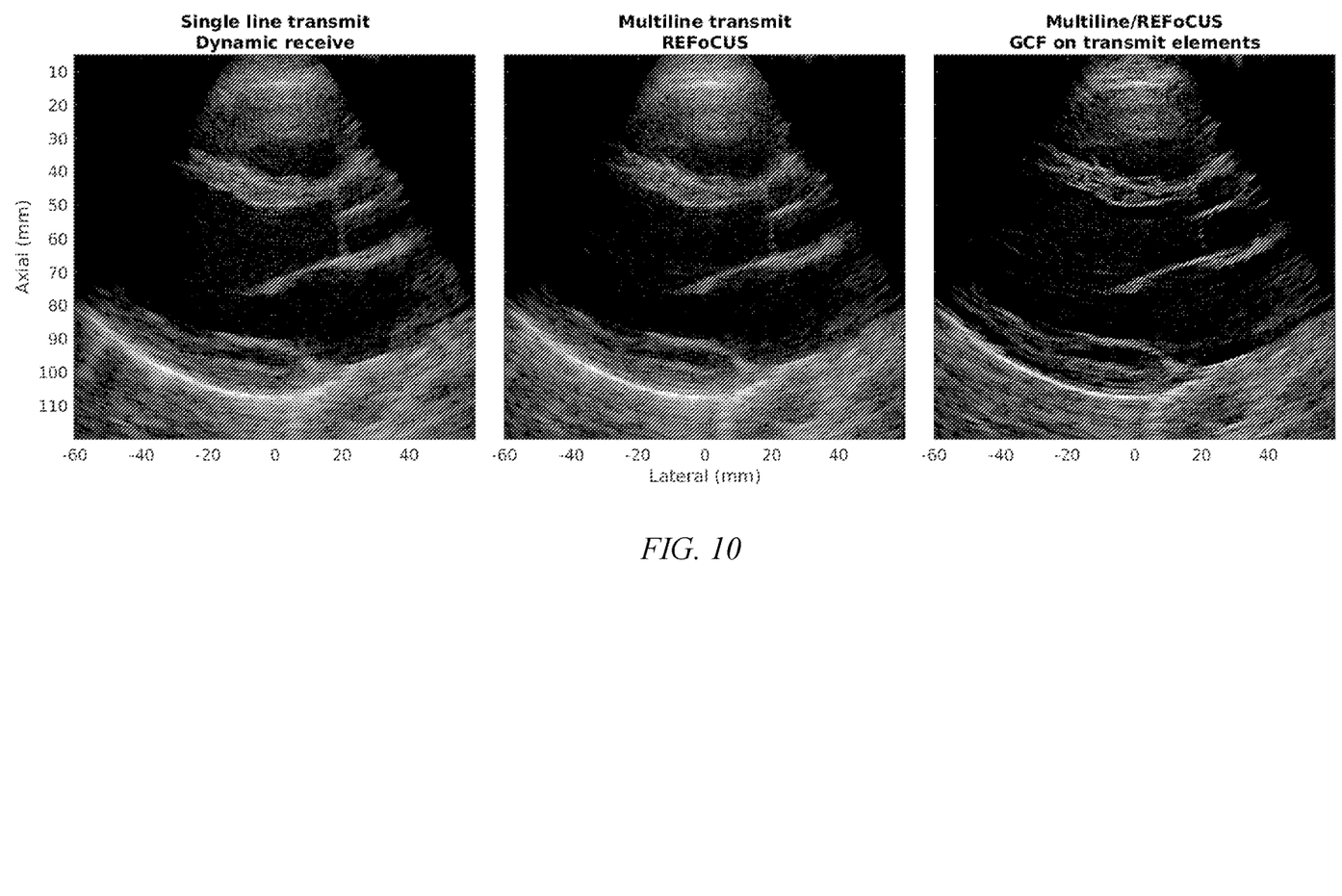
FIG. 10 is a set of three images showing the processing of in vivo cardiac data. The use of multiline transmission with four overlapping transmit beams processed with the appropriate decoding results in images with similar image quality to the single transmission case but four times the frame rate. The generalized coherence factor (GCF), an adaptive imaging method, is applied to the recovered transmit element domain to further improve image quality.

As previously indicated, post-processing can be applied to the recovered source element domain of the ultrasound dataset. This dimension of information is not normally accessible without the present invention. The recovered source element domain can be processed using several techniques used across the receive element domain, increasing the effectiveness of many of the techniques. For example, one can apply apodization (weighting) across the recovered source elements to affect the synthesized beam pattern. Time delays can be applied to each element to compensate for aberration due to varying speeds of sound in the target medium. Adaptive beamforming can be applied across the elements rather than a coherent sum, including spatial compounding (incoherent sum), non-linear combination (e.g., delay-multiply-and-sum), and coherence/covariance estimation. As an example, the right image in FIG. 10 shows an adaptive beamforming.

In a second aspect the present invention provides a second method for ultrasound imaging of a target region. The method according to the second aspect includes the steps of (1) providing an ultrasound system having an ultrasound transducer array with a plurality of ultrasound elements on the transducer array; (2) transmitting an ultrasound transmission from at least a subset of the plurality of elements of the transducer array to the target region; (3) receiving a plurality of echo signals at each of the subset of the plurality of elements of the array; (4) applying a decoding function based on the time delays between the applied pulses to at least some of the subset of the plurality of echo signals received at corresponding elements of the array; (5) modifying the time delay and steering angle and repeating steps (2)-(4) to provide an ultrasound dataset representing a recovered source element domain of the ultrasound dataset; (6) focusing and beamforming the ultrasound dataset to map time signals of the ultrasound dataset and combine channel signals to provide spatial pixel data; and (7) forming an ultrasound image from the spatial pixel data. The transmission in the transmitting step comprises a plurality of applied pulses and multiple pulses will be employed for methods according to the second aspect. Successive pulses within a transmission are emitted with a time delay. The time delay can vary between at least some of the pulses or the time delay can remain the same for pulses within a particular transmission. The time delay can be defined prior to the transmission or determined at transmission. Further, the time delays between pulses within a transmission can be randomly determined for a particular transmission. Each pulse in a particular transmission is emitted from at least a subset of the plurality of elements of the transducer array. Each echo signal is responsive to, or the result of, a particular emitted pulse. Thus, the steps of transmitting and receiving form a pulse-echo event. The sound generated during each pulse-echo event in methods according to the second aspect is sent in multiple directions from the ultrasound transducer array.

In an advantageous embodiment the time delays of each of the plurality of elements forms a time delay encoding matrix. The time delay encoding matrix can comprise delays for focused, plane or diverging transmissions. In further embodiments time delay encoding matrix can employ randomly generated time delay values. Post-processing can be applied to the recovered source element domain of the ultrasound dataset.

In a third aspect the present invention provides a method of decoding multipulse ultrasound data. The method includes the step of using a code applying a code based on time delays between a plurality of identical transmit pulses and decoding the echo signals using spatiotemporal synthetic aperture processing, wherein the decoded signals are used to form an ultrasound image from the spatial pixel data from a resulting ultrasound dataset.

In a fourth aspect the present invention provides a third method for ultrasound imaging of a target region. The method according to the fourth aspect includes the steps of (1) providing an ultrasound system having an ultrasound transducer array with a plurality of ultrasound elements on the transducer array; (2) transmitting an ultrasound transmission from at least a subset of the plurality of elements of the transducer array to the target region; (3) receiving a plurality of echo signals at each of the subset of the plurality of elements of the array; (4) modifying the defined time delays and repeating steps (2)-(3) to provide an ultrasound dataset representing a recovered source element domain of the ultrasound dataset; (5) applying a decoding function based on the applied time delays to at least some of the subset of the recovered source element domain of the ultrasound dataset; (6) focusing and beamforming the ultrasound dataset to map time signals of the ultrasound dataset and combine channel signals to provide spatial pixel data; and (7) forming an ultrasound image from the spatial pixel data.

Successive pulses within a transmission are emitted with a time delay. The time delay can vary between at least some of the pulses or the time delay can remain the same for pulses within a particular transmission. The time delay can be defined prior to the transmission or determined at transmission. Further, the time delays between pulses within a transmission can be randomly determined for a particular transmission. Each pulse in a particular transmission is emitted from at least a subset of the plurality of elements of the transducer array. Each echo signal is responsive to, or the result of, a particular emitted pulse. Thus, the steps of transmitting and receiving form a pulse-echo event. The sound generated during each pulse-echo event in methods according to the second aspect is sent in multiple directions from the ultrasound transducer array.

In certain embodiments of the method according to the fourth aspect the decoding function is a frequency-dependent regularized pseudoinverse. In an advantageous embodiment the time delays of each of the plurality of elements forms a time delay encoding matrix. The time delay encoding matrix can comprises delays for focused, plane or diverging transmissions. In further embodiments time delay encoding matrix can employ randomly generated time delay values. Post-processing can be applied to the recovered source element domain of the ultrasound dataset.

In a fifth aspect the present invention provides a fourth method for ultrasound imaging of a target region. The method according to the fifth aspect includes the steps of (1) providing an ultrasound system having an ultrasound transducer array with a plurality of ultrasound elements on the transducer array; (2) transmitting an ultrasound transmission from at least a subset of the plurality of elements of the transducer array to the target region; (3) receiving a plurality of echo signals at each of the subset of the plurality of elements of the array; (4) modifying the defined time delay and steering angle and repeating steps (2)-(3) to provide an ultrasound dataset representing a recovered source element domain of the ultrasound dataset; (5) applying a decoding function based on the applied time delays to at least some of the subset of the recovered source element domain of the ultrasound dataset; (6) focusing and beamforming the ultrasound dataset to map time signals of the ultrasound dataset and combine channel signals to provide spatial pixel data; and (7) forming an ultrasound image from the spatial pixel data.

The transmission in the transmitting step comprises a plurality of applied pulses at more than one steering angle and multiple pulses will be employed for methods according to the fifth aspect. Successive pulses within a transmission are emitted with a time delay. The time delay can vary between at least some of the pulses or the time delay can remain the same for pulses within a particular transmission. The time delay can be defined prior to the transmission or determined at transmission. Further, the time delays between pulses within a transmission can be randomly determined for a particular transmission. Each pulse in a particular transmission is emitted from at least a subset of the plurality of elements of the transducer array. Each echo signal is responsive to, or the result of, a particular emitted pulse. Thus, the steps of transmitting and receiving form a pulse-echo event and sound generated during each pulse-echo event is sent in multiple directions. The sound generated during each pulse-echo event in methods according to the fifth aspect is sent in multiple directions from the ultrasound transducer array.

In certain embodiments of the method according to the fourth aspect the decoding function is a frequency-dependent regularized pseudoinverse. In an advantageous embodiment the time delays of each of the plurality of elements forms a time delay encoding matrix. The time delay encoding matrix can comprises delays for focused, plane or diverging transmissions. In further embodiments time delay encoding matrix can employ randomly generated time delay values. Post-processing can be applied to the recovered source element domain of the ultrasound dataset.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Signal-to-noise ratio (SNR) limits image quality across all applications of ultrasound imaging. In B-mode imaging, penetration to deep targets is limited by signal attenuation through the tissue. This limitation is especially apparent in flow imaging where low-scattering blood must be separated from background tissue and system noise. SNR can be improved by increasing transmit power, but safety concerns require the limitation of peak pulse pressure and therefore achievable gains in signal amplitude. Penetration can be improved by lowering the transmit pulse frequency but at the expense of image resolution. Longer duration transmissions contain more energy and produce higher SNR but also result in reduced axial resolution proportional to the pulse length.

Coded excitation instead leverages mathematical properties of designed extended signals that allow for pulse compression in post-processing to achieve high SNR and recover sufficient axial resolution for diagnostic imaging. However, these methods face practical challenges when implemented on real hardware in complex imaging conditions.

Spatial codes have been used to improve the SNR of individual element transmissions by emitting on multiple elements simultaneously with varying amplitude, such as defined by a Hadamard matrix [R. Chiao, L. Thomas, and S. Silverstein, "Sparse array imaging with spatially-encoded transmits," 1997 IEEE Ultrasonics Symposium, pp. 1679-1682, 1997.] or S-sequence [T. Harrison, A. Samplaleanu, and R. Zemp, "S-sequence spatially encoded synthetic aperture ultrasound imaging," IEEE Transactions on Ultrasonics, Ferroelectrics, and Frequency Control, vol. 61, no. 5, pp. 886-890, 2014.], and then decoding with the inverse code. These sequences are limited in both frame rate and signal gain based on the code length, often the number of elements on the array.

Temporal codes have been demonstrated to improve SNR by increasing the time-bandwidth product of the output signal, lengthening the duration of the output while constrained by the transducer bandwidth. The most common temporal code is a linearly frequency modulation, or "chirp", that can be decoded using a matched filter—a time-reversed version of the coding signal. Chirp signals require more complex transmission systems to produce the desired output signal and are subject to effects such as frequency-dependent attenuation that necessitate more advanced decoding filters [T. Misaridis and J. Jensen, "Use of modulated excitation signals in medical ultrasound. Part I: basic concepts and expected benefits," IEEE Transactions on Ultrasonics, Ferroelectrics and Frequency Control, vol. 52, no. 2, pp. 177-191, 2005]. Binary temporal codes are a form of amplitude modulation that transmit multiple repeated pulses using +1 or −1 weightings, somewhat simplifying the transmit system. Golay codes require pairs of transmissions for decoding, making them subject to motion artifact and reducing frame rate. Barker codes and binary "pseudochirps" can be decoded with matched filters or with significantly lower range lobe levels using inverse filters [M. O'Donnell, "Coded excitation system for improving the penetration of real-time phased-array imaging systems," IEEE Transactions on Ultrasonics, Ferroelectrics and Frequency Control, vol. 39, no. 3, pp. 341-351, 1992; B. Haider, P. Lewin, and K. Thomenius, "Pulse elongation and deconvolution filtering for medical ultrasonic imaging," IEEE Transactions on Ultrasonics, Ferroelectrics and Frequency Control, vol. 45, no. 1, pp. 98-113, 1998; F. Gran, J. Udesen, M. Nielsen, and J. Jensen, "Coded ultrasound for blood flow estimation using subband processing," IEEE Transactions on Ultrasonics, Ferroelectrics and Frequency Control, vol. 55, no. 10, pp. 2211-2220, 2008.], although these codes require careful design of the inverse filter to avoid amplification of noise. Barker codes are typically limited in code length, although longer compound codes have been demonstrated with inverse filtering [E. Vienneau and B. Byram, "Compound Barker-Coded Excitation for Increased Signal-to-Noise Ratio and Penetration Depth in Transcranial Ultrasound Imaging," 2020 IEEE International Ultrasonics Symposium, September 2020.], and as an amplitude-based code are incompatible with pulse-inversion harmonic imaging.

Example 1—Improving Signal-to-Noise Ratio Through Generalized Multipulse Transmit Encoding A straightforward, robust spatiotemporal code referred to herein as multipulse encoding is presented that requires only repeated excitations with prescribed time delays. This code is robust to amplitude and frequency effects, can be easily added to existing imaging sequences, and can be decoded simultaneously with the applied focal delays to produce a synthetically two-way focused image.

Various time delay may be used. In some embodiments, the respective transmission time delay of the elements forms a time delay encoding matrix, and the time delay encoding matrix may be formed of randomly generated time delay values. By "randomly" generated, it is meant that the time delay values may be predetermined or predefined, such as by a random number generator or lookup table of random values. In some embodiments, the random values may be between a given range of values.

Time delay encoding can be employed for synthetic aperture imaging [P. Gong, M. C. Kolios, and Y. Xu, "Delay-encoded transmission and image reconstruction method in synthetic transmit aperture imaging," IEEE Transactions on Ultrasonics, Ferroelectrics, and Frequency Control, vol. 62, no. 10, pp. 1745-1756, 2015; P. Gong, M. C. Kolios, and Y. Xu, "Pseudoinverse Decoding Process in Delay-Encoded Synthetic Transmit Aperture Imaging," IEEE Transactions on Ultrasonics, Ferroelectrics, and Frequency Control, vol. 63, no. 9, pp. 1372-1379, 2016; N. Bottenus, "Recovery of the complete data set from focused transmit beams," IEEE Transactions on Ultrasonics, Ferroelectrics, and Frequency Control, vol. 65, no. 1, pp. 30-38, 2018; R. Ali, C. D. Herickhoff, D. Hyun, J. J. Dahl, and N. Bottenus, "Extending Retrospective Encoding for Robust Recovery of the Multistatic Data Set," IEEE Transactions on Ultrasonics, Ferroelectrics, and Frequency Control, vol. 67, no. 5, pp. 943-956, 2020.]. Retrospective Encoding For Conventional Ultrasound Sequences (REFOCUS) treats applied focal delays from a sequence, for example a steered plane wave sequence, as a spatial encoding of the individual transmit elements on an array [N. Bottenus, "Recovery of the complete data set from focused transmit beams," IEEE Transactions on Ultrasonics, Ferroelectrics, and Frequency Control, vol. 65, no. 1, pp. 30-38, 2018.]. The time delay $T_{n,m}$ applied to the mth element during the nth transmission is treated as a time delay encoding, which appears as a frequency-dependent phase shift in the Fourier domain. The inversion of this matrix at each frequency, whether approximated as an adjoint operation or a regularized pseudoinverse, allows for recovery of individual transmit element contributions to the recorded signal. This "complete data set" can then be processed using standard multistatic synthetic aperture focusing techniques to form a synthetically focused image. This approach differs from standard synthetic aperture focusing techniques that require assumptions about the geometry of the transmit beam in the imaging field by considering only the transducer excitation.

Figure 1:
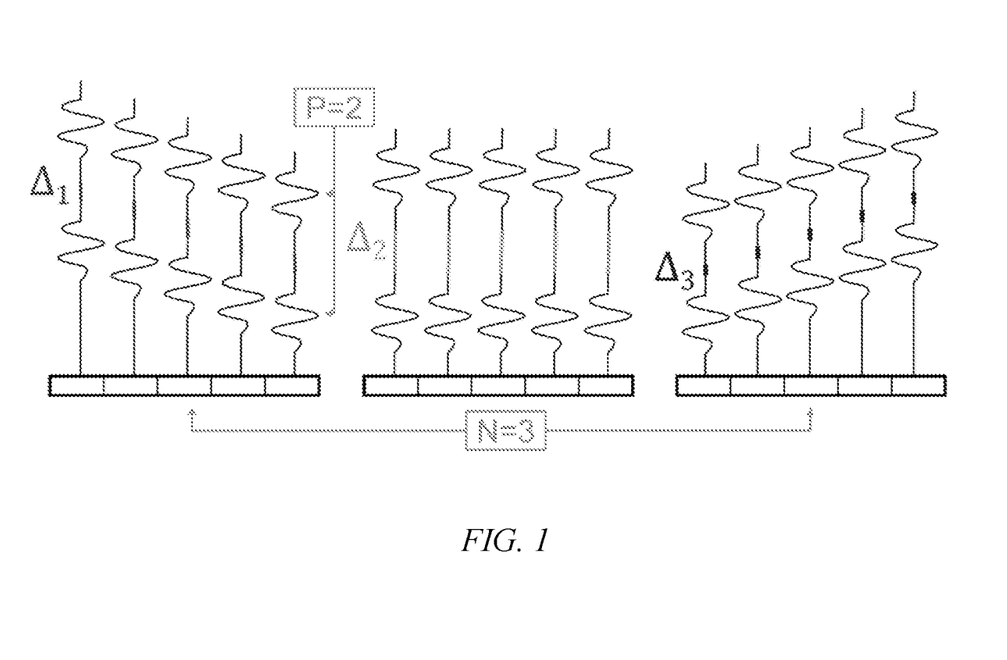
FIG. 1 is an illustration depicting a sample multi-pulse sequence with P=2 pulses repeated within each transmission, over N=3 transmissions with different plane wave steering angles. Each transmission uses a different delay delta-n between the pulses.

The present invention leverages this time delay encoding by adding more terms to each entry of the encoding matrix representing additional time-shifted transmit pulses. During each transmission in the imaging sequence, P pulses are transmitted in rapid succession on each element. FIG. 1 shows a sample sequence composed of N=3 steered plane waves where P=2 pulses are excited during each transmit event. Delays $\Delta i, n$ are placed between each pulse and varied between transmissions and pulses.

For a single transmitted pulse, the encoding matrix $H_i(\omega)$ has columns representing the M array elements combined during each of N transmissions. Each entry in the matrix consists of an amplitude apodization (here, all unity) and a phase term $e^{-j\omega T_{n,m,i}}$ corresponding to the applied time delay of the ith pulse:

$$H_i(\omega) = \begin{bmatrix} e^{-j\omega \tau_{1,1,i}} & e^{-j\omega \tau_{2,1,i}} & \ldots & e^{-j\omega \tau_{N,1,i}} \\ e^{-j\omega \tau_{1,2,i}} & e^{-j\omega \tau_{2,2,i}} & \ldots & e^{-j\omega \tau_{N,2,i}} \\ \vdots & \vdots & \ddots & \vdots \\ e^{-j\omega \tau_{1,M,i}} & e^{-j\omega \tau_{2,M,i}} & \ldots & e^{-j\omega \tau_{N,M,i}} \end{bmatrix} \quad (1)$$

$$\tau_{n,m,i} = \tau_{n,m} + \Delta_{i,n} \quad (2)$$

Each applied delay is the conventional focusing delay $\tau_{n,m}$ combined with the chosen offset $\Delta i, n$. The total encoding matrix $H(\omega)$ is given by the sum of these matrices over all transmitted pulses:

$$H(\omega) = \sum_{i=1}^{P} H_i(\omega) \quad (3)$$

One then assumes that in the Fourier domain the recorded data $S(\omega)$ is the linear combination of individual element contributions $U(\omega)$ according to this coding matrix, and that the regularized pseudoinverse of the matrix $H+(\omega)$ can be applied to decode the data.

$$S(\omega) = U(\omega) H(\omega) \quad (4)$$

$$\hat{U}(\omega) = S(\omega) H^\dagger(\omega) = U(\omega)\left(H(\omega) H^\dagger(\omega)\right) \quad (5)$$

In conventional temporal codes such as the Barker code, amplitude modulation of +1 or −1 is used to apply phase shifts of 0 or 180 degrees to the transmitted pulses in such a way that data from each individual transmit-receive event can be decoded to achieve an effective short-time, high-bandwidth, high-SNR transmit pulse. The proposed multi-pulse spatiotemporal code, given only a single amplitude (+1), does not have this same capability. Instead, the time delays between repeated pulses $\Delta i, n$ have been chosen from a uniform random distribution such that applying the pseudoinverse of $H(\omega)$ across the entire acquisition sequence provides a similar effect of pulse compression, restoring a short-time, high-bandwidth, high-SNR transmit pulse. This operation simultaneously recovers the individual transmit element contributions to allow for synthetic focusing from the complete data set, as demonstrated for REFOCUS.

TABLE I

EXPERIMENTAL PARAMETERS

| Parameter | Value |
| --- | --- |
| Transducer | P4-2v phased array |
| Elements | 64 |
| Transmit voltage | 1.6 V |
| Center frequency | 2.72 MHz |
| Focusing | Steered planewave |
| Steering angles | −45:0.5:45 degrees |
| Number of pulses (P) | [1,2,4,8,12,13,16] |
| Pulse spacing ($\Delta$) | 0.5-1.5 μsec |

Methods

This method is demonstrated experimentally using the Verasonics Vantage 256 research ultrasound scanner (Verasonics, Inc., Kirkland, WA). A steered plane wave sequence was constructed as described in Table I and used to image an ATS 539 tissue mimicking phantom (CIRS, Norfolk, VA) with point and lesion targets. Each acquisition was repeated 4 times to allow for measurement of temporal SNR using normalized cross correlation between each pair of frames [B. H. Friemel, L. N. Bohs, K. R. Nightingale, and G. E. Trahey, "Speckle decorrelation due to two-dimensional flow gradients.," IEEE transactions on ultrasonics, ferroelectrics, and frequency control, vol. 45, no. 2, pp. 317-27, 1998.]. SNR was measured using a 20 mm×20 mm speckle region centered at 90 mm depth.

The multi-pulse output was constructed by repeating the programmed transmit excitation (a single-cycle 2.72 MHz square wave, duration 0.37 μsec) with delays chosen from a uniform distribution between 0.5 and 1.5 μsec between the start of each pulse.

For comparison, a 13-bit Barker code was implemented using the same technique, omitting the additional delays between pulses and inverting the amplitude of the excitation waveform according to the code [1 1 1 1 1 −1 −1 1 1 −1 1 −1 1]. In addition to imaging the phantom, both the 13-bit Barker code and a 13-pulse multipulse transmission were used to image a 100 μm diameter nylon monofilament in a water tank to measure the axial point spread function. The Barker code data were first decoded using a 128-tap time-domain inverse filter [F. Gran, J. Udesen, M. Nielsen, and J. Jensen, "Coded ultrasound for blood flow estimation using subband processing," IEEE Transactions on Ultrasonics, Ferroelectrics and Frequency Control, vol. 55, no. 10, pp. 2211-2220, 2008], [E. Vienneau and B. Byram, "Compound Barker-Coded Excitation for Increased Signal-to-Noise Ratio and Penetration Depth in Transcranial Ultrasound Imaging," 2020 IEEE International Ultrasonics Symposium, September 2020.] then processed using REFOCUS as above, using $H_i(\omega)$ for a single transmitted pulse. For fair comparison of the SNR between techniques, the inverse filter was also used as a matched filter (i.e., using a code of [+1]) for the multipulse data before decoding using the H(ω) matrix. A regularization factor of 0.1 was used in the Tikhonov regularization in all cases.

Results

Figure 2:
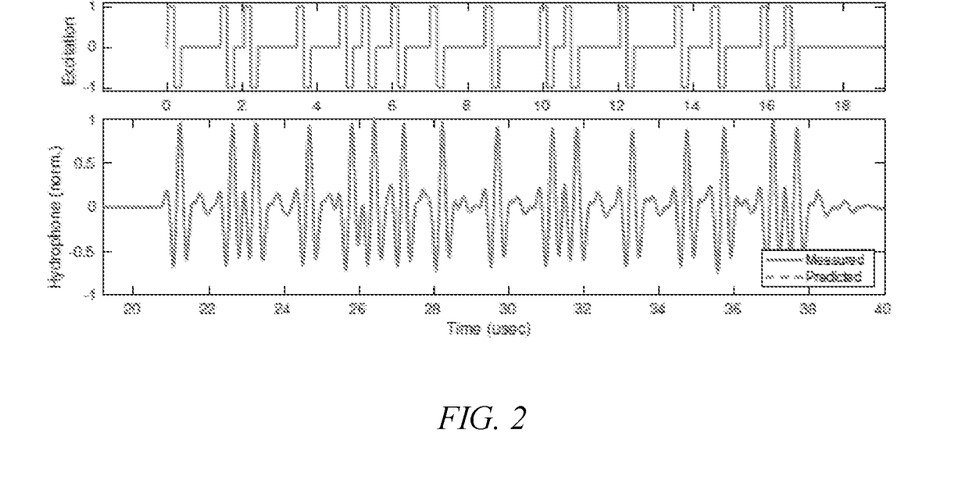
FIG. 2 is a pair of graphs. (top) Tri-state excitation showing P=16 encoding with delays varying between 0.5 and 1.5 μsec. (bottom) Normalized pressure trace from hydrophone showing pressure waveform produced by the excitation and the linear prediction based on the recording of a single output pulse. Measurement and excitation have been aligned in time for clarity.

The theory above relies on the linearity of the transmit system, including the power supply, excitation circuit, and transducer response (note, not wave propagation in the field). The linearity of the system was verified by using a hydrophone (HNC-400, Onda Corp., Sunnyvale, CA) to measure a single pulse output and a chosen 16-pulse output. FIG. 2 shows both the 16-pulse excitation waveform and the measured response. The response is overlaid with the predicted output based on time-shifting and summing the single-pulse output, showing very good agreement.

Figure 3:
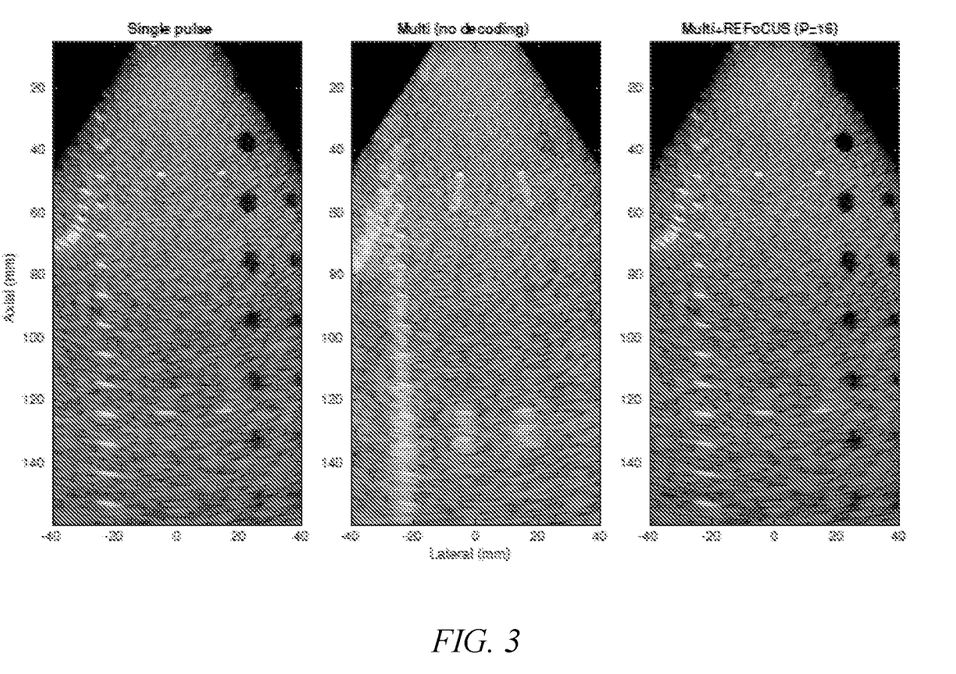
FIG. 3 is a set of three sample phantom images for (left) conventional single pulse acquisition, (middle) 16-pulse acquisition processed with conventional beamforming, and (right) 16-pulse acquisition processed with the encoding matrix of (3). The decoding accomplishes pulse compression and recovers axial resolution with high SNR.

FIG. 3 compares images from a single-pulse and a 16-pulse sequence. The middle image shows the 16-pulse data processed without the correct encoding matrix, showing the increased axial extent of the coded excitation pulse. After proper decoding, both images show comparable image quality with modest improvements in target detectability at the bottom of the 16-pulse image. Given more challenging imaging conditions (e.g., deeper, more attenuating) this difference may be more pronounced.

Figure 4:
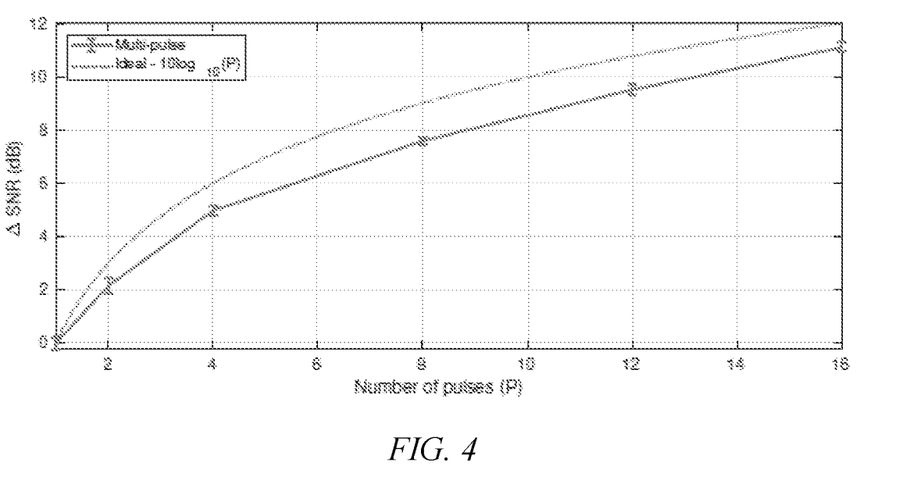
FIG. 4 is a graph showing the measured temporal SNR gain between four acquisitions as a function of number of pulses P in each output/transmission, relative to the P=1 case. The gain in signal-to-noise ratio for the processed multi-pulse image is compared to the ideal gain achieved by averaging P independent noise realizations, resulting in a 10 log 10(P) dB gain in SNR.

This difference is more clearly reflected in the gains in signal-to-noise ratio shown in FIG. 4. The gains made from increasing the number of pulses follow but do not reach the ideal limit that would be achieved by averaging the same number of independent data sets. This effect is most likely due to the imperfect encoding provided by the random time delays, which can be addressed through code design.

Figure 5:
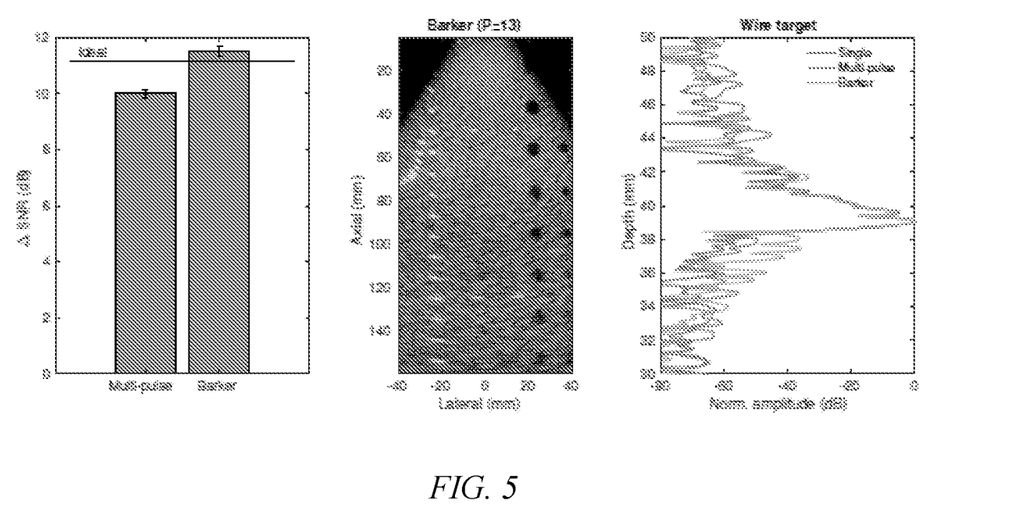
FIG. 5 is a pair of graphs and an image showing a comparison between 13-bit Barker code and P=13 multipulse encoding. (left) Comparison of SNR gain with the ideal 10 log 10(13) dB line drawn for reference. (middle) Phantom image produced using Barker code data. (right) Axial point spread function measured using 100 μm nylon monofilament in water.

In contrast, the Barker code was observed to provide more ideal SNR improvement as shown in FIG. 5. However, the observed gains actually exceeded the expected value and may indicate static noise or clutter associated with the decoding rather than gains in the signal. Both the multipulse and Barker codes were observed to provide the same axial resolution after pulse compression. The Barker code produced larger amplitude range lobes than the multipulse approach, but it also achieved a shorter extent of its range lobes. The Barker code was observed to be very sensitive to the type of decoding applied [T. Misaridis and J. Jensen, "Use of modulated excitation signals in medical ultrasound. Part I: basic concepts and expected benefits," IEEE Transactions on Ultrasonics, Ferroelectrics and Frequency Control, vol. 52, no. 2, pp. 177-191, 2005]. The relationship between the two approaches can be addressed, including at greater code lengths.

Other spatiotemporal codes such as cascaded dual-polarity waves [Y. Zhang, Y. Guo, and W. N. Lee, "Ultrafast Ultrasound Imaging with Cascaded Dual-Polarity Waves," IEEE Transactions on Medical Imaging, vol. 37, no. 4, pp. 906-917, 2018.] have been previously demonstrated, combining synthetic aperture (e.g., planewave) imaging with temporal coding (+1/−1 amplitude modulation) using pairs of transmissions for decoding without affecting frame rate. The methodology taught herein does not require inversion of the transmit pulse, simplifying the transmit system and making the encoding robust to nonlinear propagation effects. However, the multipulse strategy will result in longer excitation times due to the variable spacing between pulses, possibly resulting in a larger "dead zone" near the transducer depending on saturation of the receiving amplifiers.

The choice of Δi, n can be revised for optimum performance. We have observed but not characterized variations in SNR with the span of delays allowed, here 0.5-1.5 μsec. It is likely that given the limited number of delays used in a typical sequence, a pseudo-random code may be found that performs better than the one chosen in this study. It may even be possible to integrate other traditional codes (e.g., Hadamard, Barker, Golay, m-sequence) into this approach while retaining the flexibility of varying pulse and transmission numbers. Other approaches to delay selection are also possible, including variations between elements, but it is important to ensure that the pseudoinverse of the encoding matrix at each frequency does not amplify noise as would happen with regularly spaced pulses, for example. Similarly determined by the encoding matrix, the maximum code length achievable may be limited by the number of transmissions in the sequence.

Although not demonstrated in this study, a unique property of time-delay encoding is that it is preserved during non-linear propagation [P. Gong, P. Song, and S. Chen, "Delay-encoded Harmonic Imaging (DEHI) in Multiplanewave Compounding," IEEE Transactions on Medical Imaging, vol. 0062, no. c, pp. 952-959, 2016.]. The code should be unaffected by frequency dependent attenuation and harmonic generation, making it possible to form pulse-inversion harmonic images with improved signal-to-noise ratio using this strategy.

We have demonstrated a spatiotemporal encoding scheme to increase signal-to-noise ratio using the simplest ultrasound scanner capability—time delayed transmit pulses. This approach is simple to implement, flexible in parameter choice, and robust to effects that typically degrade coded excitations. The multipulse transmit encoding can be described by a linear systems approach and decoded simultaneously with the applied transmit delays to form a high-SNR, synthetically focused image.

Example 2—Synthetic Aperture Focusing for Multiline Transmit Beamforming

Description of purpose: Multiline transmit (MLT) imaging has been demonstrated to provide benefits in framerate by sending sound in multiple directions during a single pulse-echo event, but at the expense of "cross-talk" artifacts [A. Ramalli et al., *IEEE Trans. Ultrason. Ferroelectr. Freq. Control*, vol. 65, no. 11, pp. 2030-2041, 2018; G. Zurakhov et al., IEEE Trans. Ultrason. Ferroelectr. Freq. Control, vol. 65, no. 4, pp. 535-545, 2018; A. Ramalli, et al. *IEEE Trans. Ultrason. Ferroelectr. Freq. Control*, vol. 67, no. 5, pp. 923-933, May 2020]. These artifacts arise from the fact that the multiple transmit beams have side lobes that overlap in space, as do receive focusing beams. These result in a degradation of contrast and target detectability in reconstructed images. Several solutions have been demonstrated to reduce these artifacts, including transmit/receive apodization, adaptive beamforming, and coherence processing. We demonstrate a new approach to reconstructing these data by recognizing the MLT acquisition sequence as a spatiotemporal encoding of the array data. Decoding of these data will enable improved focusing by synthetic aperture methods and reduce cross-talk artifacts.

Figure 6:
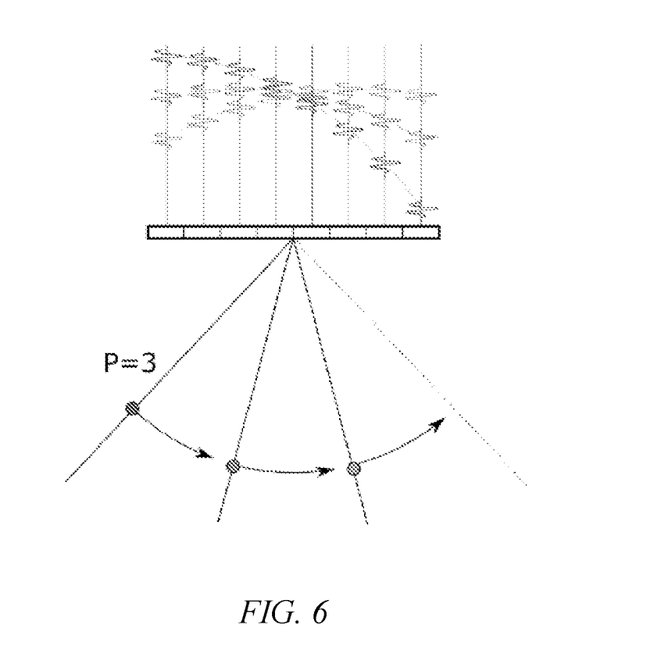
FIG. 6 is an illustration of a multiline transmit scheme for P=3 pulses. Overlapping excitations or responses of each element are linearly combined into a single emission. The arrows indicate the direction each beam is moved throughout the imaging sequence. Imaging frame rate is improved by a factor of P, but closely spaced beams may suffer from crosstalk.

Methods: We describe the multiline transmit scheme using the linear combination of multiple transmissions. Each element of the array transmits up to P unique pulses in a single transmit event with time delays determined by the P focal points selected for each transmission as illustrated in FIG. 6. The N*P focused beams that would be transmitted in a conventional imaging sequence are divided into N transmissions, improving frame rate by a factor of P.

We describe the backscattered data recorded by the array s(t) as a linear combination of the echoes corresponding to the individual transmit element signals u(t). In the frequency domain:

$$S(\omega) = U(\omega)H(\omega)$$

The encoding matrix $H(\omega)$ is the sum of encoding matrices $H_i(\omega)$, where each column of the matrix represents the time delays $\tau_{n,m,i}$ applied to each of M elements for a single transmission (N total):

$$H_i(\omega) = \begin{bmatrix} e^{-j\omega\tau_{1,1,i}} & \cdots & e^{-j\omega\tau_{N,1,i}} \\ \vdots & \ddots & \vdots \\ e^{-j\omega\tau_{1,M,i}} & \cdots & e^{-j\omega\tau_{N,M,i}} \end{bmatrix}$$

$$H(\omega) = \sum_{i=1}^{P} H_i(\omega)$$

We estimate the echoes corresponding to transmission from each of the transmit elements as if they had transmitted a single pulse using regularized pseudoinversion of the encoding matrix to produce a decoding matrix $H\dagger(\omega)$. We refer to this approach REFOCUS beamforming [N. Bottenus *IEEE Trans. Ultrason. Ferroelectr. Freq. Control*, vol. 65, no. 1, pp. 30-38, 2018; R. Ali, et al. *IEEE Trans. Ultrason. Ferroelectr. Freq. Control*, vol. 67, no. 5, pp. 943-956, May 2020]:

$$U(\omega) = S(\omega)H\dagger(\omega) = U(\omega)(H(\omega)H\dagger(\omega))$$

The individual transmit element data are then used for synthetic aperture two-way focusing:

$$sfoc(\vec{r}) = \sum \sum s(t - (\tau(\vec{r}, j) + \tau(\vec{r}, k)), j, k) Mj = 1 Mk = 1$$

The time of flight between the jth element and a point in the field $\vec{r}$ is given by $\tau(\vec{r},j)$. The expected result is an image that is transmit and receive focused throughout the field of view with high signal-to-noise ratio and low cross-talk artifacts from the multiline transmit scheme.

These methods were first tested using Field II to simulate single line transmission and MLT-4 (P=4) by linearly combining data from the complete data set composed of responses to individual transmit elements. The P4-2v phased array transducer (Verasonics, Inc., Kirkland, WA) was modeled with 64 elements, 3 MHz center frequency, and 60% fractional bandwidth. Point targets and a mixed target phantom were simulated containing both anechoic lesions and point targets in a speckle background (10 speckle realizations). A −20 dB bandlimited gaussian noise was added to the point target channel data, and −6 dB to the mixed target channel data. We modeled an imaging sequence of 180 beams over a 90 degree sector with 7 cm focus. A Tukey window was applied on transmit to reduce cross-talk between transmit beams in all cases.

We also acquired experimental phantom data using the Verasonics Vantage ultrasound scanner (Verasonics, Inc., Kirkland, WA) matching the simulation parameters. We used the ArbWave toolbox to produce the MLT-4 transmissions for each element such that overlapping excitations were linearly combined. Data were stored for offline processing.

Figure 7:
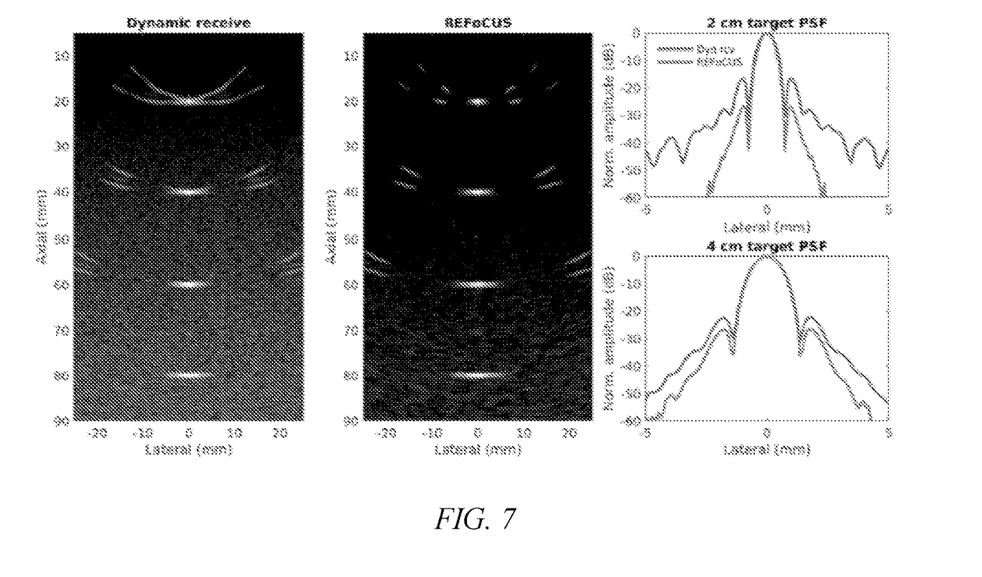
FIG. 7 is a set of two images and two graphs showing simulated point targets for (left) dynamic receive imaging and (middle) REFOCUS beam-forming for MLT-4. (right) Lateral point spread functions at two depths away from the original transmit focus (7 cm) are shown. Images shown on a 60 dB dynamic range.

Results: In simulation shown in FIG. 7, we observed significant improvement in the lateral point spread function (PSF) and improvements in the signal-to-noise ratio (SNR) through depth. We observed comparable main lobe resolution and a reduction of side lobe levels using REFOCUS to process the MLT data, as well as a reduction in amplitude of the cross-talk artifact further from the point. Cross-talk artifact in both cases could be further reduced by applying a Tukey window on receive at the expense of resolution. A Tukey window was required on transmit to suppress axial cross-talk artifacts in both cases.

Figure 8:
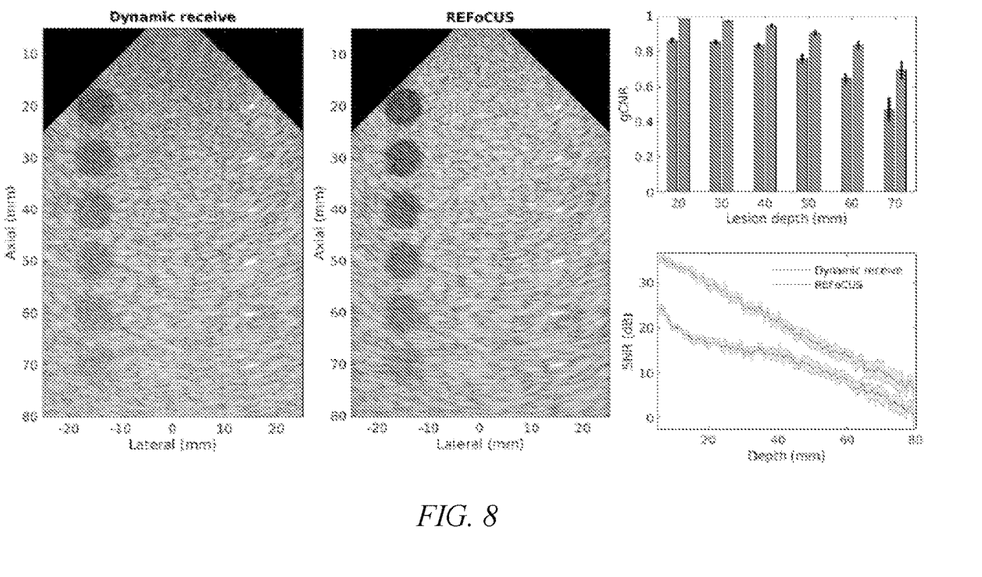
FIG. 8 is a set of two images and two graphs showing simulated mixed targets for (left) dynamic receive imaging and (middle) REFOCUS beamforming for MLT-4. (right) gCNR measured for lesion targets through depth and temporal SNR measured on the beamsum data through depth. Error bars represent measurement over 5 noise realizations and 10 speckle realizations. Images shown on a 60 dB dynamic range.

The simulated mixed target phantom is shown in FIG. 8, showing significant improvements in lesion detectability as indicated by the gCNR metric and SNR as measured by the temporal correlation between noise realizations. Focusing improvement was most impactful near the transducer, where the transmit beams were broad. The largest gains in SNR were observed in the near-field where the transmit beams are poorly focused compared to near the 7 cm focal depth, but the impact of improved SNR could be most clearly observed at depth where it limits target detectability in the dynamic receive case.

Figure 9:
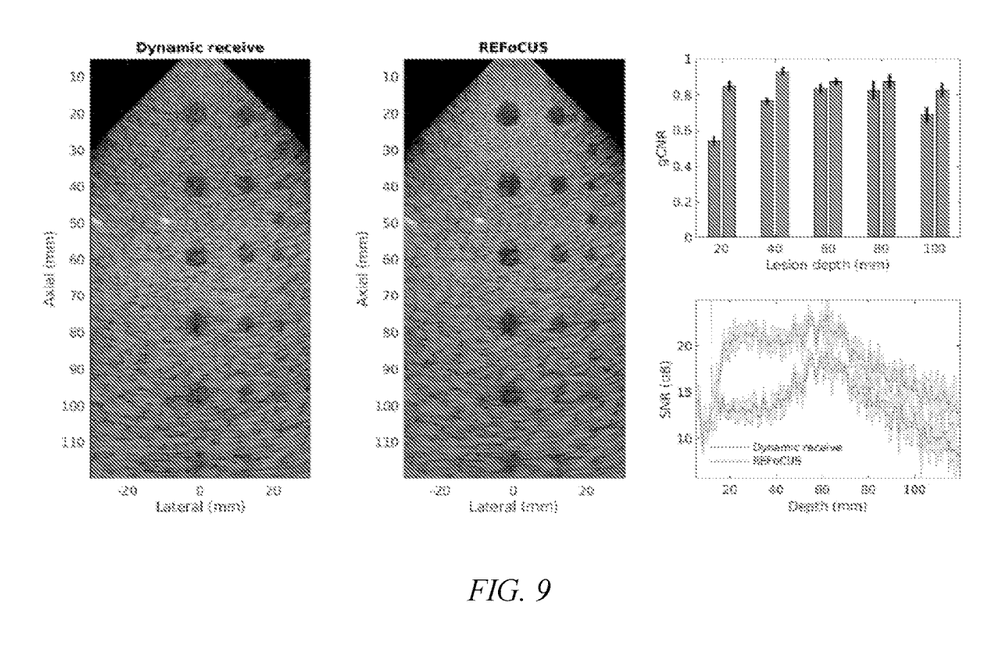
FIG. 9 is a set of two images and two graphs showing experimental phantom targets for (left) dynamic receive imaging and (middle) REFOCUS beamforming for MLT-4. (right) gCNR measured for lesion targets through depth and temporal SNR measured on the beamsum data through depth. Error bars represent measurement over 4 noise realizations and 4 speckle realizations. Images shown on a 60 dB dynamic range.

Experimental data in FIG. 9 shows improvements in both focusing and signal-to-noise ratio due to REFOCUS processing of the MLT data. Lesion detectability near the focus showed only modest improvements, but SNR was improved through depth and gCNR was improved significantly away from the 7 cm transmit focus.

We present an original beamforming strategy for multiline transmission ultrasound data that recognizes it as time delay encoded and performs an appropriate decoding to reduce common reconstruction artifacts. This approach simultaneously enables synthetic aperture focusing of multiline transmission data for the first time, improving focusing through depth.

We have demonstrated a synthetic aperture method for improved focusing of multiline transmit ultrasound data. REFOCUS beamforming performs an inversion of the time delay encoding applied during parallel transmission of multiple steered beams. We observed improved lesion detectability and depth penetration in both simulation and experiments using this method.

Glossary

The present invention has been described with reference to the accompanying drawings and examples, in which embodiments of the invention are shown. This invention may, however, be embodied in many different forms and should not be construed as limited to the embodiments set forth herein. Rather, the embodiments are provided to ensure that the disclosure is thorough and complete, and fully conveys the scope of the invention to those skilled in the art.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

As used throughout the entire application, the terms "a" and "an" are used in the sense that they mean "at least one", "at least a first", "one or more" or "a plurality" of the referenced components or steps, unless the context clearly dictates otherwise. For example, the term "an agent" includes a plurality of agents, including mixtures thereof.

The term "and/or" wherever used herein includes the meaning of "and", "or" and "all or any other combination of the elements connected by said term".

The term "about" or "approximately" as used herein means within 20%, preferably within 10%, and more preferably within 5% of a given value or range.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range. All references to the function log default to e as the base (natural log) unless stated otherwise (such as $\log_{10}$).

As used herein, the term "comprising" is intended to mean that the products, compositions and methods include the referenced components or steps, but not excluding others. "Consisting essentially of" when used to define products, compositions and methods, shall mean excluding other components or steps of any essential significance. Thus, a composition consisting essentially of the recited components would not exclude trace contaminants and pharmaceutically acceptable carriers. "Consisting of" shall mean excluding more than trace elements of other components or steps.

As used herein, the phrases "for example," "for instance," "such as," or "including" are meant to introduce examples that further clarify more general subject matter. These examples are provided only as an aid for understanding the disclosure, and are not meant to be limiting in any fashion.

As used herein, the terms "may," "optional," "optionally," or "may optionally" mean that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

Common numbers refer to common elements throughout the specification and appended drawings. In the figures, the thickness of lines, layers, components, elements or features may be enhanced for clarity.

The terminology used herein is for the purpose of describing particular embodiments and is not intended to be limiting of the invention.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under." The device may be otherwise oriented (rotated 90 degrees or at other orientations) and the spatially relative descriptors used herein interpreted accordingly. Similarly, the terms "upwardly," "downwardly," "vertical," "horizontal" and the like are used herein for the purpose of explanation only unless specifically indicated otherwise.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present invention. The sequence of operations (or steps) is not limited to the order presented in the claims or figures unless specifically indicated otherwise.

By "defined time delay" it is meant that the time delay is a known time delay between pulses in a transmission where the time of the delay is determined at or prior to a transmission.

The present invention can be described with reference to block diagrams and/or flowchart illustrations of methods, apparatus (systems) and/or computer program products according to embodiments of the invention. It is understood that each block of the block diagrams and/or flowchart illustrations, and combinations of blocks in the block diagrams and/or flowchart illustrations, can be implemented by computer program instructions. These computer program instructions may be provided to a processor of a general-purpose computer, special-purpose computer, and/or other programmable data processing apparatus to produce a machine, such that the instructions, which execute via the processor of the computer and/or other programmable data processing apparatus, create means for implementing the functions/acts specified in the block diagrams and/or flowchart block or blocks.

These computer program instructions may also be stored in a computer-readable memory that can direct a computer or other programmable data processing apparatus to function in a particular manner, such that the instructions stored in the computer-readable memory produce an article of manufacture including instructions which implement the function/act specified in the block diagrams and/or flowchart block or blocks.

The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions/acts specified in the block diagrams and/or flowchart block or blocks.

Accordingly, the present invention may be embodied in hardware and/or in software (including firmware, resident software, micro-code, etc.). Furthermore, embodiments of the present invention may take the form of a computer program product on a computer-usable or computer-readable non-transient storage medium having computer-usable or computer-readable program code embodied in the medium for use by or in connection with an instruction execution system.

The computer-usable or computer-readable medium may be, for example but not limited to, an electronic, optical, electromagnetic, infrared, or semiconductor system, apparatus, or device. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM).

It will be understood that the scope of the present invention includes, for example, two-dimensional (2D) ultrasound imaging and 3D (or volumetric) ultrasound imaging. In addition, the components of the ultrasound imaging described herein may be packaged as a single unit or packaged separately and interconnected to provide the functions described herein.

As used herein the term "method" and/or "system: refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

All references cited in the present application are incorporated in their entirety herein by reference to the extent not inconsistent herewith.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A method for ultrasound imaging of a target region comprising the steps of:
   a. providing an ultrasound system having an ultrasound transducer array with a plurality of ultrasound elements on the transducer array;
   b. transmitting an ultrasound transmission from at least a subset of the plurality of elements of the transducer array to the target region, wherein the transmission comprises a plurality of pulses and successive pulses are emitted with a defined time delay that varies between at least some of the pulses, wherein each pulse is emitted from at least a subset of the plurality of elements of the transducer array;
   c. receiving a plurality of echo signals at each of the subset of the plurality of elements of the array, each echo signal being responsive to the respective emitted pulse;
   d. applying a decoding function based on the applied time delays to at least some of the subset of the plurality of echo signals received at corresponding elements of the array;
   e. modifying the defined time delays and repeating steps (b)-(d) to provide an ultrasound dataset representing a recovered source element domain of the ultrasound dataset;

f. focusing and beamforming the ultrasound dataset to map time signals of the ultrasound dataset and combine channel signals to provide spatial pixel data; and g. forming an ultrasound image from the spatial pixel data.

2. The method for ultrasound imaging of a target region according to claim 1, wherein the time delays of each of the plurality of elements forms a time delay encoding matrix.

3. The method for ultrasound imaging of a target region according to claim 2, wherein the time delay encoding matrix comprises delays for focused, plane or diverging transmissions.

4. The method for ultrasound imaging of a target region according to claim 2, wherein the time delay encoding matrix comprises randomly generated time delay values.

5. The method for ultrasound imaging of a target region according to claim 2, wherein the time delay encoding matrix is modified to avoid overlapping pulse excitations in time.

6. The method for ultrasound imaging of a target region according to claim 1, the method further comprising applying post-processing on the recovered source element domain of the ultrasound dataset.

7. A method for ultrasound imaging of a target region comprising the steps of:
a. providing an ultrasound system having an ultrasound transducer array with a plurality of ultrasound elements on the transducer array;
b. transmitting an ultrasound transmission from at least a subset of the plurality of elements of the transducer array to the target region, wherein the transmission comprises a plurality of pulses and successive pulses are emitted with a defined time delay that varies between pulses, wherein each pulse is emitted from at least a subset of the plurality of elements of the transducer array;
c. receiving a plurality of echo signals at each of the subset of the plurality of elements of the array, each echo signal being responsive to the emitted pulses, wherein the steps of transmitting and receiving form a pulse-echo event and sound generated during each pulse-echo event is sent in multiple directions;
d. applying a decoding function based on the defined time delays to at least some of the subset of the plurality of echo signals received at corresponding elements of the array;
e. modifying the defined time delay and steering angle and repeating steps (b)-(d) to provide an ultrasound dataset representing a recovered source element domain of the ultrasound dataset;
f. focusing and beamforming the ultrasound dataset to map time signals of the ultrasound dataset and combine channel signals to provide spatial pixel data; and
g. forming an ultrasound image from the spatial pixel data.

8. The method for ultrasound imaging of a target region according to claim 7, wherein the time delays of each of the plurality of elements forms a time delay encoding matrix.

9. The method for ultrasound imaging of a target region according to claim 8, wherein the time delay encoding matrix comprises delays for focused, plane or diverging transmissions.

10. The method for ultrasound imaging of a target region according to claim 8, wherein the time delay encoding matrix is modified to avoid overlapping pulse excitations in time.

11. The method for ultrasound imaging of a target region according to claim 7, the method further comprising applying post-processing on the recovered source element domain of the ultrasound dataset.

12. A method for ultrasound imaging of a target region comprising the steps of:
a. providing an ultrasound system having an ultrasound transducer array with a plurality of ultrasound elements on the transducer array;
b. transmitting an ultrasound transmission from at least a subset of the plurality of elements of the transducer array to the target region, wherein the transmission comprises a plurality of pulses and successive pulses are emitted with a defined time delay that varies between at least some of the pulses, wherein each pulse is emitted from at least a subset of the plurality of elements of the transducer array;
c. receiving a plurality of echo signals at each of the subset of the plurality of elements of the array, each echo signal being responsive to the emitted pulses;
d. modifying the defined time delays and repeating steps (b)-(c) to provide an ultrasound dataset representing a recovered source element domain of the ultrasound dataset;
e. applying a decoding function based on the applied time delays to at least some of the subset of the recovered source element domain of the ultrasound dataset;
f. focusing and beamforming the ultrasound dataset to map time signals of the ultrasound dataset and combine channel signals to provide spatial pixel data; and
g. forming an ultrasound image from the spatial pixel data.

13. The method for ultrasound imaging of a target region according to claim 12 wherein the decoding function is a frequency-dependent regularized pseudoinverse.

14. The method for ultrasound imaging of a target region according to claim 13, wherein the time delays of each of the plurality of elements forms a time delay encoding matrix.

15. The method for ultrasound imaging of a target region according to claim 14, wherein the time delay encoding matrix comprises delays for focused, plane or diverging transmissions.

16. The method for ultrasound imaging of a target region according to claim 14, wherein the time delay encoding matrix is modified to avoid overlapping pulse excitations in time.

17. The method for ultrasound imaging of a target region according to claim 12, the method further comprising applying post-processing on the recovered source element domain of the ultrasound dataset.

18. A method for ultrasound imaging of a target region comprising the steps of:
a. providing an ultrasound system having an ultrasound transducer array with a plurality of ultrasound elements on the transducer array;
b. transmitting an ultrasound transmission from at least a subset of the plurality of elements of the transducer array to the target region, wherein the transmission comprises a plurality of pulses at more than one steering angle and successive pulses are emitted with a defined time delay that varies between pulses, wherein each pulse is emitted from at least a subset of the plurality of elements of the transducer array;
c. receiving a plurality of echo signals at each of the subset of the plurality of elements of the array, each echo signal being responsive to the emitted pulses, wherein the steps of transmitting and receiving form a pulse-echo event and sound generated during each pulse-echo event is sent in multiple directions;
d. modifying the defined time delay and steering angle and repeating steps (b)-(c) to provide an ultrasound dataset representing a recovered source element domain of the ultrasound dataset;
e. applying a decoding function based on the applied time delays to at least some of the subset of the recovered source element domain of the ultrasound dataset;
f. focusing and beamforming the ultrasound dataset to map time signals of the ultrasound dataset and combine channel signals to provide spatial pixel data; and
g. forming an ultrasound image from the spatial pixel data.

19. The method for ultrasound imaging of a target region according to claim 18 wherein the decoding function is a frequency-dependent regularized pseudoinverse.

20. The method for ultrasound imaging of a target region according to claim 18, wherein the time delays of each of the plurality of elements forms a time delay encoding matrix.

21. The method for ultrasound imaging of a target region according to claim 20, wherein the time delay encoding matrix comprises delays for focused, plane or diverging transmissions.

22. The method for ultrasound imaging of a target region according to claim 20, wherein the time delay encoding matrix is modified to avoid overlapping pulse excitations in time.

23. The method for ultrasound imaging of a target region according to claim 18, the method further comprising applying post-processing on the recovered source element domain of the ultrasound dataset.

* * * * *